United States Patent
Poelker et al.

(10) Patent No.: US 7,284,610 B2
(45) Date of Patent: *Oct. 23, 2007

(54) POLYAMINE SALTS AS CLAY STABILIZING AGENTS

(75) Inventors: David J. Poelker, Missouri City, TX (US); Joann McMahon, Arnold, MO (US); John A. Schield, Missouri City, TX (US)

(73) Assignee: Baker Hughes Incorporated, Houston, TX (US)

( * ) Notice: Subject to any disclaimer, the term of this patent is extended or adjusted under 35 U.S.C. 154(b) by 305 days.

This patent is subject to a terminal disclaimer.

(21) Appl. No.: 11/010,759

(22) Filed: Dec. 13, 2004

(65) Prior Publication Data

US 2005/0126782 A1 Jun. 16, 2005

Related U.S. Application Data

(60) Provisional application No. 60/529,992, filed on Dec. 16, 2003.

(51) Int. Cl.
*E21B 33/138* (2006.01)
(52) U.S. Cl. ...................... 166/294; 166/300
(58) Field of Classification Search ............ None
See application file for complete search history.

(56) References Cited

U.S. PATENT DOCUMENTS

| | | | |
|---|---|---|---|
| 3,920,698 A * | 11/1975 | Haemmerle et al. | 548/546 |
| 4,366,074 A * | 12/1982 | McLaughlin et al. | 507/222 |
| 4,532,052 A * | 7/1985 | Weaver et al. | 507/222 |
| 4,812,244 A | 3/1989 | Lawson et al. | |
| 5,160,642 A * | 11/1992 | Schield et al. | 507/222 |
| 6,287,458 B1 * | 9/2001 | Lawrence | 210/91 |

2004/0235677 A1   11/2004   Nguyen

OTHER PUBLICATIONS

"Clay Master-5C Product Information", BJ Services Company, May 1996, pp. 1-2.
"Clay Treat-3C Product Information", BJ Services Company, May 1996.
"Aquet Ay 80 Clay Stabilizer Product Data", Baker Hughes, Feb. 1999, p. 1.
"FSA-1 Product Information", BJ Services Company, Jul. 24, 2000, pp. 1-2.
"Ammonium Chloride Product Information", BJ Services Company, Oct. 31, 2000, pp. 1-2.
"Halliburton's Solution to Highly Reactive Clay Formation Challenges," PetroMin, Jul. 2003, pp. 52-53.
United Nations Environmental Programme, "3-Aminopropyldimethylamine: CAS No. 109-55-7" [Internet], OECD Screening Information Data Sheets (SIDS) (cited Sep. 2003) Available from: http://www.chem.unep.ch/irptc/sids/oecdsids/109557.pdf.
T. Higuchi, "Thesis: Chapter Two: Review of Previous Work," University of Durham, Stockton-on-Tees, United Kindom, Available from: http://www.dur.ac.uk/toru/higuchi/wfi/toru_thesis/CHAPTER%202.doc.
PCT International Search Report for PCT/US2004/042034, May 6, 2005.

* cited by examiner

*Primary Examiner*—Zakiya Bates
*Assistant Examiner*—Angela DiTrani
(74) *Attorney, Agent, or Firm*—Madan Mossman & Sriram PC

(57) ABSTRACT

A clayish subterranean formation, such as may be encountered in rock surrounding a well bore during hydrocarbon recovery operations may be stabilized with a polyamine salt of an imide of polymaleic anhydride. The salt may be unneutralized or partially neutralized. The invention is particularly relevant to hydraulic fracturing fluids used in enhanced oil recovery. The compositions of this invention are more environmentally friendly than some current technology.

13 Claims, 3 Drawing Sheets

US 7,284,610 B2

POLYAMINE SALTS AS CLAY STABILIZING AGENTS

CROSS-REFERENCE TO RELATED APPLICATION

This application claims the benefit of U.S. provisional application No. 60/529,992 filed Dec. 16, 2003.

FIELD OF THE INVENTION

The invention relates to methods for the stabilization of clay formations, particularly those encountered in the drilling of and production from hydrocarbon wells, and most particularly relates, in one non-limiting embodiment, to methods and compositions useful to stabilize such clay formations.

BACKGROUND OF THE INVENTION

Production of petroleum hydrocarbons is often troubled by the presence of clays and other fines capable of migrating in the formation. Normally, these fines, including the clays, are quiescent, causing no obstruction of flow to the well bore via the capillary system of the formation. However, when the fines are disturbed, they begin to migrate in the production stream and, too frequently, they encounter a constriction in the capillary where they bridge off and severely diminish the flow rate.

A phenomenon that disturbs the quiescent fines is often the introduction of water foreign to the formation. The foreign water is often fresh or relatively fresh water compared to the native formation brine. The water is frequently intentionally introduced for purposes of hydraulic fracturing of the formation rock to increase production rates. In any event, the change in the water can cause fines to disperse from their repository or come loose from adhesion to capillary walls.

Sometimes the loss of permeability is due to clay swelling with relatively fresh water without migration. But, often clay swelling is accompanied by migration of fines. Sometimes non-swelling clays can respond to the foreign water and begin to migrate. It is believed that swelling clays are the major mechanism of fines migration and/or swelling, because when formation cores are analyzed, the presence of swelling clays are an excellent indicator that the formation will be sensitive to foreign water intrusion, while the presence of non-swelling clays only is inconclusive.

Generally, swelling clays are in the smectic group including clay minerals such as montmorillonite, beidellite, nontronite, saponite, hectorite, and sauconite. Of these, montmorillonite is the clay mineral found most commonly in formation core analysis. Montmorillonite is commonly associated with clay minerals known as mixed-layer clays.

Migrating fines including a host of clay and other minerals in minute particle size, for example, feldspars, fine silica, allophane, biotite, talc, illite, chlorite and the swelling clays themselves. Further information is found in U.S. Pat. No. 5,160,642, incorporated by reference herein in its entirety.

Clays can also cause trouble in areas other than permeability reduction. When they are a component in shales, sandstones, or other formations, contact with a foreign water or at times with any water can cause the formation to lose strength or even disintegrate. This is a problem in building foundations, road beds, drilling wells, enhanced oil recovery and any situation where the formation strength is important.

There have been numerous attempts to control the ill effects of water on clay and/or other fines. These have been principally in the oil exploration and production industry.

One idea is to convert the clay from the swelling sodium form or the more rare swelling lithium form to another cation form which does not swell as much.

Example cations that form relatively non-swelling clays are potassium, calcium, ammonium and hydrogen ions, such as from potassium chloride, ammonium chloride and the like. When a solution of these cations, mixed or individually, flows past a clay mineral, they readily replace the sodium ion and the clay is transformed to a relatively non-swelling form. The use of acid, potassium, calcium, or ammonium ions to exchange for sodium ion has been successful in preventing damage to formations susceptible to plugging or disintegrating due to clays in their compositions.

One specific approach is that of U.S. Pat. No. 4,366,074 which teaches the use of a very wide variety of polymers, including poly(acrylamide-3-propyltrimethyl-ammonium chloride) as clay stabilizers. While the illustrated compound is effective in shallow wells, it decomposes and loses its effectiveness at the higher temperatures encountered in deep wells.

Another approach teaches the use of quaternary salts of copolymers of an unsaturated acid or anhydride (including maleic anhydride) and another unsaturated compound (hydrocarbon, ester, or either), in a ratio of 1:1 to 1:4. While these materials are operable, they do not provide as high a degree of stabilization as is desired.

An alternative technique uses two polymeric additives, one that is a flocculant at low concentrations, where the other prevents hydration and disintegration of clay-rich formations. Water-soluble, organosilicone compounds have also been used to reduce the mobility of clay and other siliceous fines in clayish formations.

U.S. Pat. No. 5,160,642 to Schield, et al. instructs that a clayish formation, such as encountered in rock surrounding an oil well bore, is stabilized with a quaternary ammonium salt of an imide of polymaleic anhydride. The method is particularly relevant to hydraulic fracturing fluids used in enhanced oil recovery.

Accordingly, it would be desirable to provide a clay stabilization composition that would provide a high degree of stabilization and that would not decompose at the temperatures encountered in deep oil wells, or if it did decompose would decompose into components that would present little or no toxicity concerns.

SUMMARY OF THE INVENTION

An object of the invention is to provide an effective method for clay stabilization.

Other objects of the invention include providing a method for stabilizing clays during drilling and production from oil wells.

Another object of the invention is to provide a composition for stabilizing clays that can be readily produced.

In carrying out these and other objects of the invention, there is provided, in one form, a composition that includes an amine salt of an imide of a polymer of maleic anhydride selected from the group consisting of homopolymers of maleic anhydride and copolymers of maleic anhydride containing repeating units at least about 90% of which are maleic anhydride. The polyamine may be optionally at least partially neutralized with an acid to form the salt.

In another non-limiting embodiment of the invention there is provided a method of stabilizing a clay-containing formation comprising contacting the formation with a composition comprising an amine salt of an imide of a polymer of maleic anhydride selected from the group consisting of homopolymers of maleic anhydride and copolymers of maleic anhydride containing repeating units at least about 90% of which are maleic anhydride. The polyamine may be optionally at least partially neutralized with an acid to form the salt.

In another non-restrictive embodiment of the invention, there are provided novel polyamine salts having the structure:

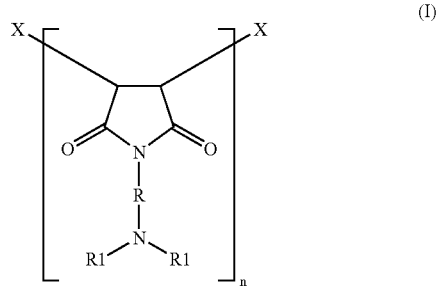

where n ranges between 2 and 5, inclusive, X is independently selected from the group consisting of $(R1)_2N-R-NH-$, $HO-(CH_2)_x-O-$, and $HO-$, x ranges between 2 and 5, inclusive, R is an alkylene radical of 1 to 12 carbon atoms and R1 are each independently selected from the group consisting of H and alkyl radicals of 1 to 12 carbon atoms.

DETAILED DESCRIPTION OF THE INVENTION

Figure 1:
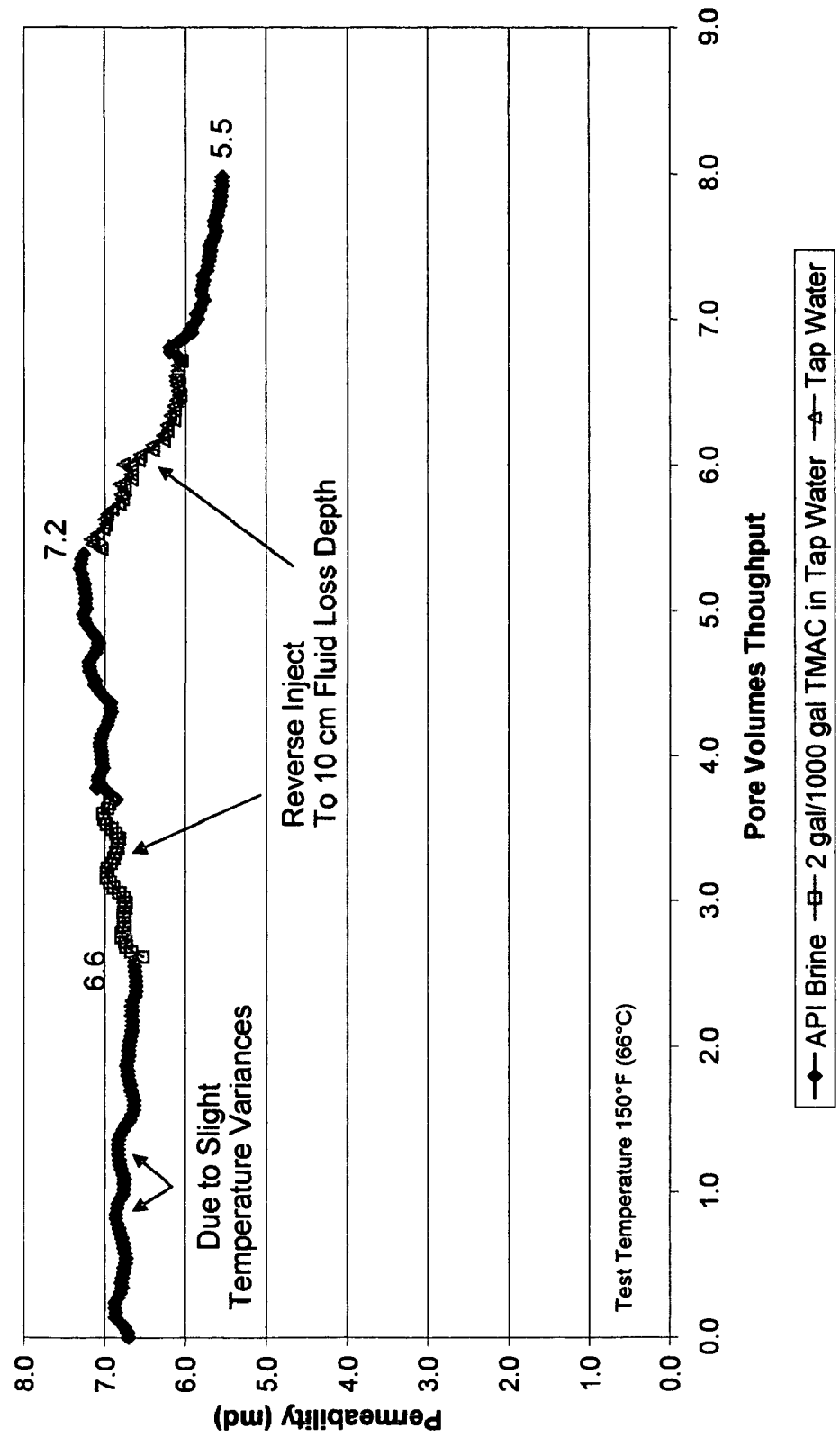
FIG. 1 is a graph of the effect of TMAC and Tap Water on the permeability of Bandera Sandstone at 150° F. (66° C.)

It has been discovered that compositions containing amine salts of imides of maleic anhydride polymers are useful for clay stabilization during hydrocarbon exploration and recovery operations, as well as other operations.

A first component useful in the invention is maleic anhydride:

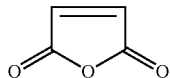

Maleic anhydride is well known to those skilled in the art and is widely commercially available. It will be appreciated that other organic anhydrides may find utility as reactants in making the amine salts of this invention.

The maleic anhydride is polymerized to form a homopolymer. By use of the term "homopolymer" herein the reference is likewise to encompass impliedly a polymer in which there is not a significant or large amount of another component. Of course, most commercial grades of maleic anhydride may contain some quantity of other polymerizable compounds, and it would be possible (although not necessarily advisable) to add trivial amounts of another unsaturated compound. What is important is that the quantity of other components in the polymer be sufficiently low that the performance of the polymer is not significantly impaired for the stated function herein. Generally, the polymer will be at least 90%, alternatively at least 92%, in one non-limiting embodiment at least 94%, in another non-restrictive version at least 96%, in another non-limiting embodiment at least 98% and alternatively at least 99% composed of repeating units of maleic anhydride. Thus, while the term "homopolymer" is used herein for conciseness, the compositions and techniques should be recognized to be applicable to such limited copolymers as well.

In one non-limiting embodiment of the invention, the maleic anhydride is reacted with a tertiary amine to yield a polymer having the general structure:

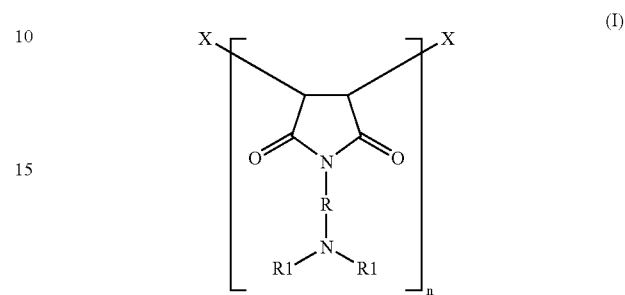

where n ranges between 2 and 5, inclusive, and X is independently selected from the group consisting of $(R1)_2N-R-NH-$, $HO-(CH_2)_x-O-$, and $HO-$, and x ranges between 2 and 5, inclusive, R is an alkylene radical, in one non-limiting embodiment unbranched, having 1 to 12, or 2 to 8, possibly 2 to 6, alternatively 2 to 4 carbon atoms, and in another non-limiting embodiment 3 carbon atoms. Each R1 are independently selected from the group consisting of H and alkyl radicals of 1 to 12 inclusive, or 1 to 8, possibly 1 to 4, and alternatively 1 to 3 carbon atoms. In one non-limiting embodiment of the invention, at least one of the R1 groups is alkyl, or in the alternative both are alkyl.

While the higher molecular weights (i.e., n=6 to 100, or more) would be expected to be operable, such polymers are generally difficult to produce. The lower molecular weights (i.e., n=2 to 5) are useful because of their relative ease of manufacture. In one non-limiting embodiment of the invention, the reaction is catalyzed by the tertiary nitrogen in a tertiary amine co-reactant. This reaction may be schematically represented as:

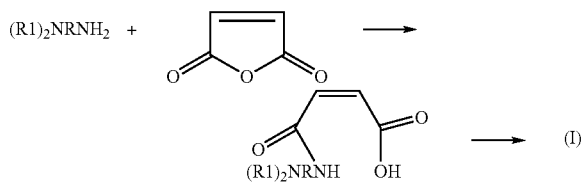

where R and R1 have the same definitions as above.

In another non-limiting embodiment of the invention, the polymerization may takes place using a free radical catalyst. Suitable free radical catalysts include, but are not necessarily limited to, peroxides such as hydrogen peroxide, t-butyl peroxide, t-butyl hydroperoxide, and cumene hydroperoxide; persulfates such as sodium persulfate, potassium persulfate, and ammonium persulfate; and azo compounds such as azobisisobutyronitrile. Generally, a catalyst will be present at 0.01 to 25, alternatively 0.1 to 20, and possibly 1 to 15 weight percent, based on the weight of the monomer.

The polymerization reaction may take place at any suitable temperature, for instance at 50° C. to 250° C., and in another non-limiting embodiment, at 100° C. to 200° C. The use of a polymerization catalyst is optional, and if no catalyst is used, the polymerization temperature may range from about 90° C. to about 175° C., and in another non-limiting embodiment, from about 105° C. to about 160° C.

If a catalyst is used, the polymer will usually be such that the molecular weight will correspond to n being from 5 to 7.

If no catalyst is used (i.e., only heat is used to drive the polymerization) n will be from 2 to 5.

The polymerization may take place in a solvent, in one non-limiting embodiment. Suitable solvents include, but are not necessarily limited to such solvents as ethylene glycol, diethylene glycol dimethyl ether, 2-methoxyethanol, 2-butoxyethanol, propylene glycol, di(ethylene glycol) butyl ether, di(ethylene glycol) methyl ether, 1- or 2-butanol, methyl pentanols, 2-ethyl hexanol, and the like and mixtures thereof. In the possibility where X in formula (I) is HO—$(CH_2)_x$—O— or HO—, these possibilities exists because of the solvent used. The polymerization reaction will generally be complete in about 1 to about 20 hours, in another non-limiting embodiment, from about 2 to about 10 hours.

As noted, in one embodiment of the invention, the polymerization of the maleic anhydride is catalyzed by the tertiary nitrogen of the amine co-reactant, and thus a moiety of the tertiary amine generally becomes part of each maleic anhydride moiety in an approximately stoichiometric ratio. In one non-limiting embodiment of the invention, the tertiary amine has the formula $(R1)_2NRNH_2$, where R and R1 have the definitions for formula (I), above. In one non-limiting embodiment of the invention R is —$(CH_2)_3$—, and in an alternate embodiment, R1 is methyl in both instances. Suitable specific tertiary amines include, but are not necessarily limited to, 3-dimethylaminopropylamine (DMAPA), also known as N,N-dimethyl-1,3-dia-minopro-pane or 3-aminopropyldimethylamine), 3-diethylaminopropylamine, 3-dibutylaminopropylamine, and the like and mixtures thereof. In the case where in the tertiary amine definition $(R1)_2NRNH_2$, where R is —$(CH_2)_3$— and R1 is methyl in both instances, the tertiary amine is DMAPA.

In one non-limiting embodiment of the invention, it is desirable that the amine used be relatively non-toxic or of low toxicity compared to some of the currently used clay stabilizers. In the event the amine salts break down into their component parts, which is a possibility in many environments, the amine should be relatively benign. DMAPA is moderately toxic to freshwater algae (72 hour EC50 56 mg/l), fish (122 mg/l) and daphnia (60 mg/l). It is also readily degradable (about 65%) in fresh water. The 72-hr EC50 to Skeletonema growth rate is estimated to be >100 mg/L. The amine salts of this invention have very favorable toxicity properties to saltwater algae.

With respect to reactant proportions, in one non-limiting embodiment of the invention, the molar ratio of anhydride to tertiary amine may range from about 1:100 to about 100:1, alternatively from about 1:50 to about 50:1, and in another non-limiting embodiment may range from about 2:1 to about 1:2.

It is within the scope of this invention to use an acid to at least partially neutralize the amine to form the salt. Relatively mild acids, such as organic acids, may be used in one non-limiting embodiment of the invention, but stronger acids, such as mineral acids, might find utility in some applications. If and when the amine salt dissociates, it may be desirable to have relatively milder acids result for a number of reasons including, but not necessarily limited to, limiting corrosion, reducing toxicity, etc. Some specific, suitable acids include, but are not necessarily limited to methanesulfonic acid, glycolic acid, sulfuric acid, hydrochloric acid, hydrofluoric acid, sulfurous acid, and the like and mixtures thereof. Generally, the industry is moving away from using halide acids such as hydrochloric acid and hydrofluoric acid.

In one non-limiting embodiment of the invention, the imide of the invention is not neutralized, that is, when the pH is about 9.3. In one non-restrictive form, it has been surprisingly discovered that these polyamine salts are effective even at high pH when the amine salts are not cationically charged, but neutral. In another embodiment of the invention, enough acid should be employed to at least partially neutralize the amine and form a salt. In one non-limiting embodiment of the invention, this is approximately a 1:1 molar ratio of acid to amine groups on the polyamine. In an alternate non-limiting embodiment, the pH may be adjusted to at least about 5 or lower, or alternatively to at least about 4 or lower. Full or complete neutralization would give a pH for these salts at about 2.5. Typical drilling fluids range in pH from about 2 to about 10, but at pH of about 4, corrosion becomes an undesirable problem. At this point for the method of this invention, one non-restrictive neutralization is about 62%, thus in one non-limiting embodiment the neutralization of the polyamine ranges from 0 to about 62%, alternatively up to about 62%. Alternative, non-limiting upper thresholds are 60% and 65%.

It will be appreciated that other techniques for making the amine salts of formula (I) of this invention are suitable, including, but not necessarily limited to, polymerizing the anhydride first, and then reacting the anhydride polymer with an amine, such as a tertiary amine, to make the amine salts herein.

In use, the fluid containing the composition of the invention is contacted with the clay to be stabilized in a conventional manner, such as by injecting the fluid under pressure into the well bore. The compositions of the invention are particularly suitable for use in water-based hydraulic fracturing fluids which are injected into oil wells under very high pressure to cause the rock of the oil formation to crack, leaving channels for the oil to flow to the well bore.

It is difficult to predict with much accuracy what the proportion of amine salt in the composition should be since the appropriate dose or proportion will depend upon a number of complex, interrelated factors including, but not necessarily limited to the nature of the amine salt, the nature of the subterranean clay-containing formation, the temperature of the formation, the pressure at which the composition is introduced into the formation, etc. Nevertheless, in order to give some idea of the proportions of amine salt that may be used commercially, the amine salt may range from about 0.01 to about 0.5 wt % of the composition in one non-limiting embodiment. In another, alternate, non-limiting embodiment of the invention, the amine salt proportion may range from about 0.1 to about 0.25 wt % of the composition. The balance of the composition is expected to be water or brine, but small amounts of other additives such as corrosion inhibitors, scale inhibitors, hydrogen sulfide scavengers and the like may optionally be included.

The invention will be further illustrated by the following examples which are not intended to limit the invention, but simply to further illuminate it.

EXAMPLE 1

Preparation of Amine Salt with DMAPA and Maleic Anhydride

A 500 ml round bottom flask was charged with 60.4 g (0.592 mole) of dimethylaminopropylamine (DMAPA) and 42 g of ethylene glycol. Addition of 48.3 g (0.493 mole) of maleic anhydride was made in small portions over a 45 minute period. The temperature of the reaction mixture was maintained at less than 100° C. during the addition. After all the maleic anhydride had been added, the reaction mixture was heated to 120° C. and maintained at that temperature for 6 hours. The resulting dark reddish solution was cooled to 80° C. and diluted by addition of 89.8 g of water. TGA, thermal gravimetric analysis, of this material shows this chemistry to be stable to 400° F. This material was neutralized slowly with (48.3 g, 0.35 mole) 70% methanesulfonic acid to a pH of 4 and was given the designation A4840. The same material neutralized with acetic acid was designated A4819.

EXAMPLE 2

Figure 2:
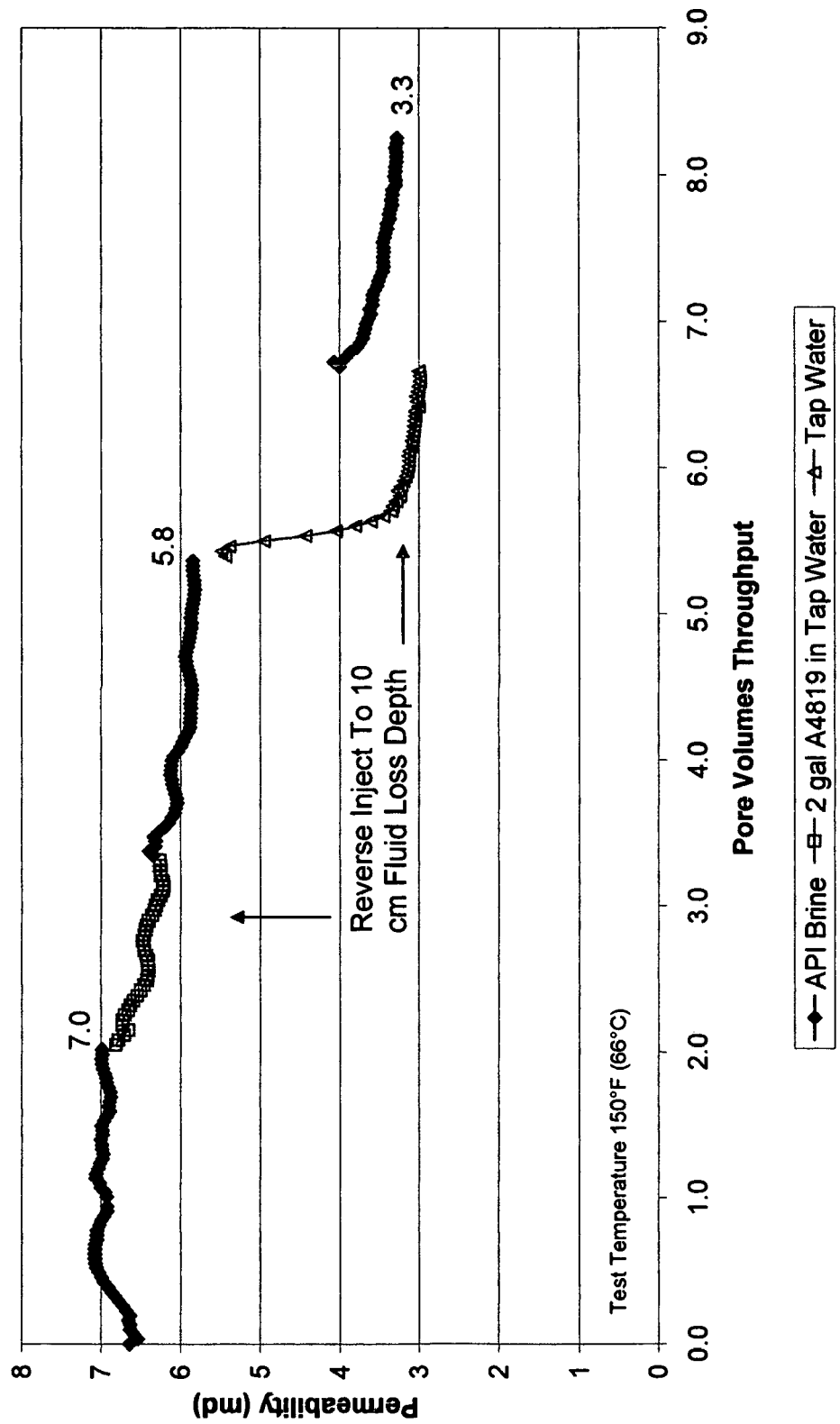
FIG. 2 is a graph of the effect of A4819 and Tap Water on the permeability of Bandera Sandstone at 150° F. (66° C.)
Figure 3:
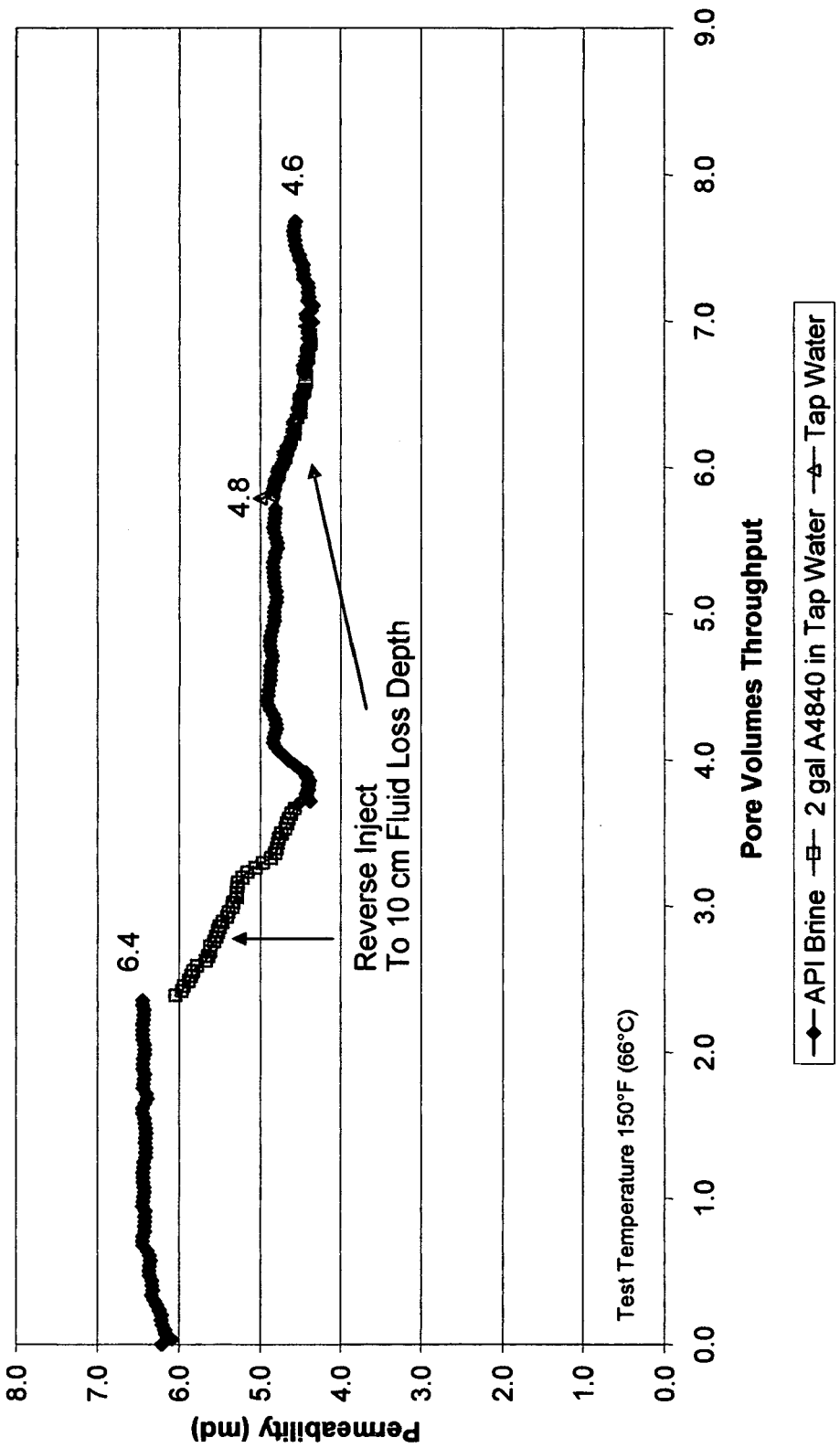
FIG. 3 is a graph of the effect of A4840 and Tap Water on the permeability of Bandera Sandstone at 150° F. (66° C.).

The products TMAC (tetramethylammonium chloride), A4819 and A4840 were tested along an API standard brine and tap water on Bandera sandstone for permeability. The results are shown in FIGS. 1, 2 and 3, respectively. While the conventional product TMAC performed well as shown in FIG. 1, so did A4819, as seen in FIG. 2 at maintaining permeability—a measure that the clay is stable. The performance in FIG. 3 for A4840 was somewhat less but still showed ability to stabilize clay.

Many modifications may be made in the composition and method of this invention without departing from the spirit and scope thereof that are defined only in the appended claims. For example, the exact combination of amine, anhydride, solvent and acid and their proportions may be different from those used here. Additionally, the polyamine salts and methods of this invention may find utility in the processes different from those explicitly discussed. The use of other components in the polyamine salt compositions of this invention not precisely identified may also fall within the inventive scope herein.

We claim:

1. A method of stabilizing a clay-containing formation comprising contacting the formation with a composition comprising a polyamine salt of an imide of a polymer of maleic anhydride selected from the group consisting of homopolymers of maleic an hydride and copolymers of maleic anhydride containing repeating units at least about 90% of which are maleic anhydride, where the polyamine salt is at least partially neutralized with an acid.

2. The method of claim 1 where the polyamine salt is neutralized up to about 65%.

3. The method of claim 1 where the acid is selected from the group consisting of glycolic acid, methanesulfonic acid, sulfurous acid, and mixtures thereof.

4. The method of claim 1 where the mole ratio of acid to amine groups on the polyamine is about 1:1.

5. The method of claim 1 where the polyamine salt has the general structure:

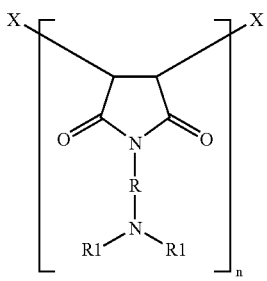

(I)

where n ranges between 2 and 5, inclusive, X is independently selected from the group consisting of $(R1)_2N-R-NH-$, $HO-(CH_2)_X-O-$, and $HO-$, x ranges between 2 and 5, inclusive, R is an alkylene radical of 1 to 12 carbon atoms and R1 are each independently selected from the group consisting of H and alkyl radicals of 1 to 12 carbon atoms.

6. The method of claim 5 where R is $-(CH_2)_3-$.

7. The method of claim 6 where each R1 is methyl.

8. The method of claim 1 where the polyamine salt is made by reacting a dialkylaminoalkylamine with maleic anhydride.

9. The method of claim 1 where the polyamine salt is made by reacting a dimethylaminopropylamine with maleic anhydride.

10. The method of claim 1 where the proportion of polyamine salt in the composition ranges from about 0.01 to about 0.5 wt %.

11. A method of stabilizing a clay-containing formation comprising contacting the formation with a composition comprising a polyamine salt of an imide of a polymer of maleic anhydride selected from the group consisting of homopolymers of maleic an hydride and copolymers of maleic anhydride containing repeating units at least about 90% of which are maleic anhydride, where the polyamine salt is neutralized up to about 65% with an acid, and where the proportion of polyamine salt in the composition ranges from about 0.01 to about 0.5 wt %.

12. The method of claim 11 where the acid is selected from the group consisting of glycolic acid, methanesulfonic acid, sulfurous acid, and mixtures thereof.

13. The method of claim 11 where the polyamine salt has the general structure:

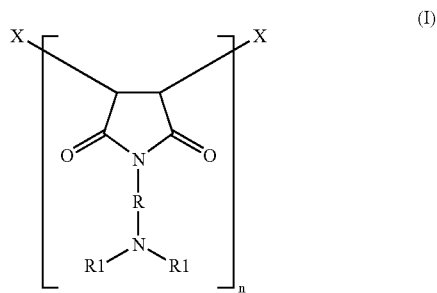

(I)

where n ranges between 2 and 5, inclusive, X is independently selected from the group consisting of $(R1)_2N-R-NH-$, $HO-(CH_2)_X-O-$, and $HO-$, x ranges between 2 and 5, inclusive, R is an alkylene radical of 1 to 12 carbon atoms and R1 are each independently selected from the group consisting of H and alkyl radicals of 1 to 12 carbon atoms.

* * * * *

UNITED STATES PATENT AND TRADEMARK OFFICE
CERTIFICATE OF CORRECTION

| | | |
|---|---|---|
| PATENT NO. | : 7,284,610 B2 | Page 1 of 1 |
| APPLICATION NO. | : 11/010759 | |
| DATED | : October 23, 2007 | |
| INVENTOR(S) | : David J. Poelker, Joann McMahon and John A. Schield | |

It is certified that error appears in the above-identified patent and that said Letters Patent is hereby corrected as shown below:

Claim 1: at column 7, line 30

Delete "an hydride" and insert therefor -- anhydride --.

Claim 11: at column 8, line 24

Delete "an hydride" and insert therefor -- anhydride --.

Signed and Sealed this

Twenty-fifth Day of December, 2007

JON W. DUDAS
*Director of the United States Patent and Trademark Office*